(12) United States Patent
Sachdeva

(10) Patent No.: US 7,252,509 B2
(45) Date of Patent: Aug. 7, 2007

(54) TOOTH TEMPLATES FOR BRACKET POSITIONING AND OTHER USES

(75) Inventor: Rohit Sachdeva, Plano, TX (US)

(73) Assignee: OraMetrix, Inc., Richardson, TX (US)

( * ) Notice: Subject to any disclaimer, the term of this patent is extended or adjusted under 35 U.S.C. 154(b) by 290 days.

(21) Appl. No.: 11/103,332

(22) Filed: Apr. 11, 2005

(65) Prior Publication Data

US 2005/0239013 A1 Oct. 27, 2005

Related U.S. Application Data

(63) Continuation-in-part of application No. 10/246,172, filed on Sep. 17, 2002, now Pat. No. 6,905,337.

(51) Int. Cl.
*A61C 5/00* (2006.01)

(52) U.S. Cl. .......................... 433/229; 433/24

(58) Field of Classification Search ................. 433/229
See application file for complete search history.

(56) References Cited

U.S. PATENT DOCUMENTS 5,863,198 A * 1/1999 Doyle ........................ 433/3
5,879,158 A * 3/1999 Doyle et al. .................. 433/24
6,554,613 B1 * 4/2003 Sachdeva et al. ............. 433/24

* cited by examiner

*Primary Examiner*—Cris Rodriguez
*Assistant Examiner*—Candice C. Stokes
(74) *Attorney, Agent, or Firm*—McDonnell, Boehnen Hulbert & Berghoff LLP

(57) ABSTRACT

Templates are disclosed that permit an orthodontist to accurately place appliances such as bracket shims or brackets on a tooth or teeth at a desired position. The templates can be used for accurately locating the position of other dental or orthodontic procedures, such as varnishing, tooth etching and root canals. The templates are made from a flexible sheet of material adapted to be adhered directly to the surface of the tooth or teeth. The sheet of material is formed with the outline of the tooth or teeth or in the shape of the tooth to allow the template to be posited in a proper, reference position. The sheet of material is also formed with one or more marks indicating the location of the bracket on the tooth, for example one mark indicting the bracket base location and other marks indicating the orientation of the base and bracket slot. The mark indicating the bracket base is punched out or otherwise removed from the sheet to provide a void in the template, enabling the user to directly bond the bracket to the tooth at the location of the void. Also disclosed is a method of verifying the accuracy of the placement of the template on the teeth of a patient.

16 Claims, 9 Drawing Sheets

Fig. 13A    Fig. 13B    Fig. 13C

TOOTH TEMPLATES FOR BRACKET POSITIONING AND OTHER USES

CROSS-REFERENCE TO RELATED APPLICATIONS

This application is a continuation-in-part application of the U.S. patent application Ser. No. 10/246,172, filed Sep. 17, 2002 now U.S. Pat. No. 6,905,337, the entire contents of which are fully incorporated by reference herein.

BACKGROUND OF THE INVENTION

A. Field of the Invention

This invention relates generally to the field of orthodontics and dentistry. More particularly, the invention relates to templates that are applied to teeth and which provide a locating mechanism for a variety of purposes, including localization of treatments on a tooth, and accurately placing brackets, bracket bonding pads, and other orthodontic appliances on teeth.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

In conventional orthodontics, accurate placement of the brackets on the teeth is important to ensure that the tooth is moved over the course of treatment to the desired finish position. The proper location of brackets on the teeth is part of treatment planning for the patient performed by the orthodontist. Desired bracket position can be determined in a variety of ways, including mathematical calculation (see Lemchen, U.S. Pat. RE 35,169 and Andreiko et al., U.S. Pat. Nos. 5,431,562 and 5,683,243), using interactive orthodontic treatment planning software (see published PCT application of OraMetrix, Inc., WO 01/80761), using wax set-ups from a model of the malocclusion, and by the orthodontist mentally visualizing the bracket placement on the tooth.

Once the desired bracket position is determined using any of these means, the actual placement of the bracket on the teeth can be carried out directly by bonding the bracket to the teeth, either with or without some bracket placement aids. Bracket placement aids, in the form of customized machined bracket placement jigs and thermoplastic bracket transfer trays, are known in the art. See the above-cited patents to Andreiko, Cohen et al. U.S. Pat. No. 3,738,005 and Cleary et al., U.S. Pat. No. 6,123,544.

The present invention provides for tooth templates for a variety of possible purposes, including precisely locating brackets on teeth. The templates represent a less costly, easier to use approach to bracket placement than the jigs and transfer trays described above. Moreover, the manufacture of the templates, at least in some embodiments, does not require any specialized equipment such as milling machines or stereolithography machines. The templates can also be used for a variety of other dental uses besides bracket placement, including a locating mechanisms for specific procedures on teeth such as varnishing and etching, treatment of cavities, root canals and other treatments.

SUMMARY OF THE INVENTION

In a first aspect, an orthodontic template for use in assisting a user in placing an appliance on a tooth is provided. The appliance may be, for example, a bracket or a bracket shim. A bracket shim is an intermediary structure with opposed surfaces, one facing the tooth and the other facing the bracket base, providing a shim between the tooth surface and the bracket base to accurately position the bracket, and in particular the slot of the bracket, in three-dimensional space. The template comprises a flexible sheet of material sized and shaped so as to be able to be placed onto at least one tooth of a set of teeth of a patient. The sheet of material has one or more marks indicating the location and orientation of where the appliance is to be placed on the at least one tooth. The sheet of material further has a tooth-facing surface adapted to be positioned on a surface of the tooth in a reference position wherein the mark accurately indicates the proper location for the appliance. The template, in some embodiments, is temporarily adhered to the surface of the tooth. In use, after the template is generated, the user removes the mark indicating the location of the appliance, creating a void in the template at that location. Alternatively, the void can be formed in the template during manufacture of the template, e.g., by stamping out the template. The template is then applied to the tooth. The void provides an aperture in the template allowing the user to directly bond a bracket to the tooth surface at that location, or, alternatively the shim. The mark applied to the sheet of material may optionally provide orientation features which assist the user in the proper placement of the bracket on the tooth.

The template can take the form of an elongate strip of material for providing a template for placing brackets on a plurality of teeth for an upper or lower arch of the patient. Alternatively, the template can take the form a single tooth template for placing a bracket on a single tooth. Other alternative constructions of the template are contemplated, such as templates that provide a feature which can be activated after the template is applied to the tooth or teeth to make a physical bracket locating mark on the tooth surface directly.

The flexible sheet of material that forms the base of the template could take a variety of forms, such as paper, plastic or other suitable material with an adhesive backing, capable of being fed through a standard, off-the shelf printer so as to print the mark onto the sheet of material. Alternatively, the flexible sheet of material could be printed without the adhesive backing and an adhesive could be applied after printing. The flexible sheet of material could be opaque or transparent, such as a transparent plastic sheet. The template can be made through other known processes, including stamping the template from a sheet of template material such as plastic.

In another preferred aspect, a method is provided for verifying the accuracy of the placement of an orthodontic template on the teeth of a patient, comprising the steps of: a) creating a design of an orthodontic template through treatment planning using a computer containing a three-dimensional virtual model of the teeth of a patient and the location of virtual appliances on the three-dimensional virtual model; b) generating the orthodontic template using the design of the orthodontic template; the template comprising a flexible sheet of material and indicating the outline of the teeth and marks indicating the position and orientation of the appliance on each tooth; c) applying the template to the surface of the actual teeth of the patient; d) verifying the accuracy of the placement of the template on the actual teeth of the patient using the computer; and e) adjusting the placement of the template on the actual teeth of the patient until the desired or acceptable placement of the template is achieved. In order to verify the accuracy of the placement of the template on the teeth of the patient, an image of the dentition of the patient with the template placed upon the teeth is taken and stored in the computer; then digitally compared with the template design placed on the virtual three-dimensional model of the teeth of the patient. If there is a discrepancy between the actual placement of the template on the teeth and the desired placement of the template, then the actual placement is adjusted until the desired or acceptable placement is achieved. The image of the dentition of the patient with the template placed upon the actual teeth is taken using in-vivo scanning or with digital photographs or by other similar means.

In another aspect, a method is provided for placing a bracket on a tooth, comprising the steps of: a) generating a template for positioning a bracket on a tooth, the template comprising a flexible sheet of material and a mark indicating the position and orientation of an appliance on the tooth and a void in the template; c) applying the template to the surface of the tooth; d) placing a bracket on the tooth at the location of the void; e) bonding a bracket or bracket shim to the tooth; and f) removing the template. In one possible embodiment, prior to the step of bonding the bracket to the tooth, the orthodontist may use the void in the template as a means for accurately applying a chemical composition to tooth surface, such as an acid or sealant, or using the void to provide a mask for laser etching of the tooth surface.

In still another aspect, a template is provided for use in applying a treatment to a tooth. The template includes a flexible sheet of material sized and shaped so as to be placeable onto at least one tooth of a set of teeth of a patient. The template has a void at the location and orientation of where a treatment is to occur on the at least one tooth. The sheet of material has a tooth-facing surface adapted to be adhered to a surface of said tooth in a reference position wherein the void accurately indicates the location of wherein the treatment is to occur. The treatment could be any possible treatments, for example, varnishing, etching, cleaning, locating a dental prosthetics e.g., crown or filling, root canal, or of course bracket placement.

The templates of this invention can be used directly on the tooth for direct bonding of the bracket, or they can be used with a model of the teeth and used to fabricate a more convention indirect bonding bracket placement jig, as discussed in detail below.

In another preferred aspect, a method of making an orthodontic template for a patient for use in assisting a user in placing an appliance on a designated tooth void of an appliance whereas each of a plurality of the remaining teeth has an appliance attached thereto is disclosed. The method comprises the steps of: (a) obtaining a three-dimensional virtual model of a patient comprising a designated tooth void of an appliance and the remaining teeth wherein each of a plurality of the remaining teeth has an appliance attached thereto; (b) storing the three-dimensional virtual model in a computer, the computer having instructions foe treatment planning and a library of virtual appliances; (c) positioning a virtual appliance on the designated tooth through treatment planning using the three-dimensional virtual model, wherein the virtual appliance is selected from the library of virtual appliances; (d) creating a design of an orthodontic template using the positioning of the virtual appliance on the designated tooth using the computer; (e) generating said orthodontic template from a flexible sheet of material using the design of the orthodontic template; the template indicating the outline of the designated tooth; and (f) sizing and shaping the flexible sheet of material so as to be able to be placed onto the designated tooth of the patient, the sheet of material having one or more marks indicating the location and orientation of where the appliance is to be placed on the designated tooth; the sheet of material having a tooth-facing surface adapted for positioning on the surface of said designated tooth in a reference position wherein the one or more marks accurately indicate the proper location for said appliance. The method is particularly useful where the designated tooth was previously only partially erupted and therefore unable to receive an appliance. The virtual three-dimensional model is created using images obtained through in-vivo scanning the patient. The images include the patient's teeth as well as existing appliances on the remaining teeth.

These and still other aspects of the invention will be more apparent from the following detailed discussion of presently preferred embodiments of the invention.

BRIEF DESCRIPTION OF THE DRAWINGS

Presently preferred embodiments of the invention are described below in reference to the appended drawings, wherein like reference numerals refer to like elements in the various views, and in which:

FIGS. 13A-D are several views of an alternative embodiment using two templates to bond an appliance to a tooth.

FIGS. 19A and 19B are used as illustrations to aid in the discussion of a method of making an orthodontic template to enable placing of an appliance on a designated tooth void of an appliance whereas the remaining teeth have existing appliances placed up on them.

DETAILED DESCRIPTION OF PREFERRED EMBODIMENTS

Figure 1:
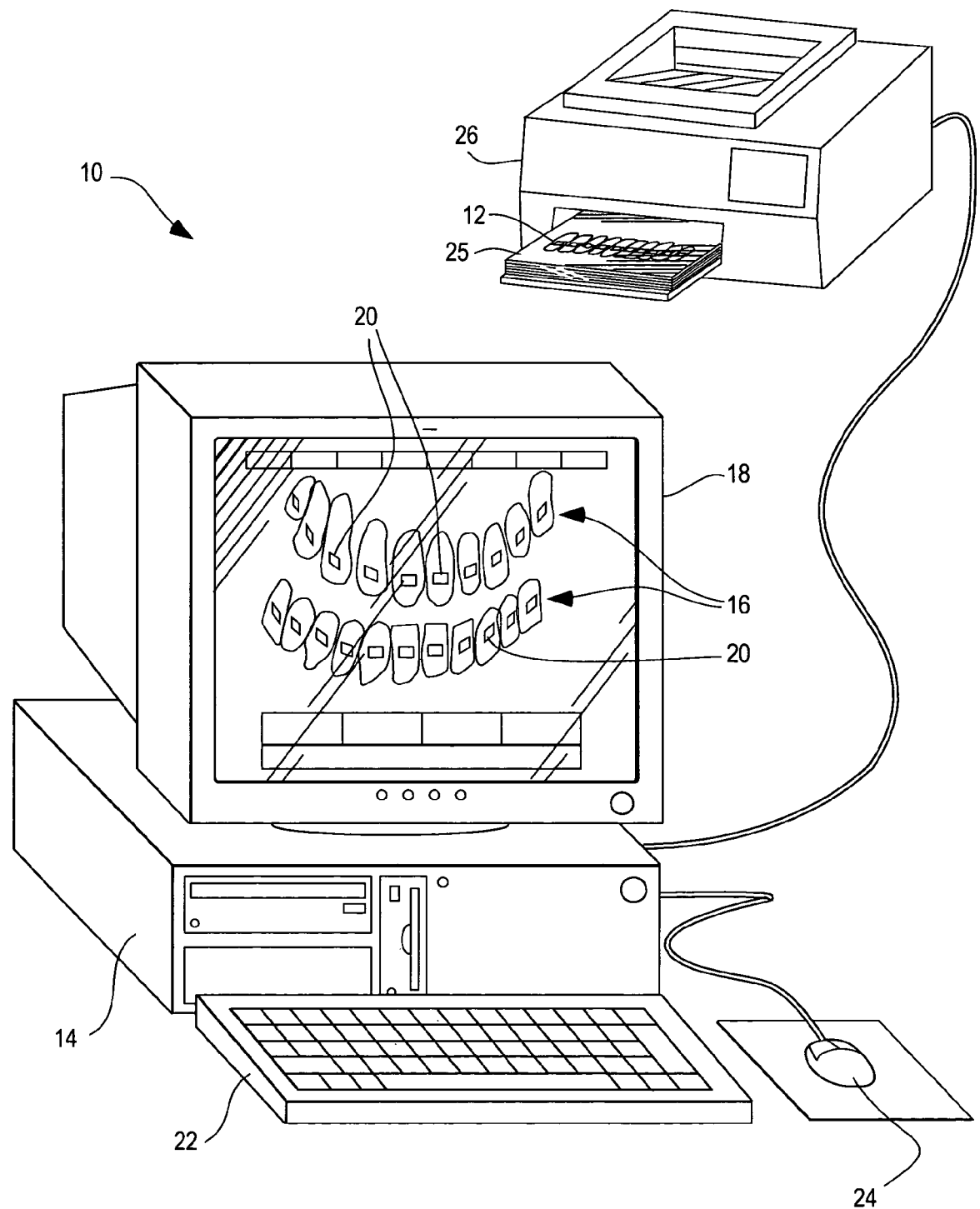
FIG. 1 is a illustration of a computer system displaying a three-dimensional virtual model of the teeth with brackets placed in a desired location thereon; the computer is connected to a printer what prints a full scale image of the teeth and bracket positions on a flexible sheet for use as a template for placing the brackets at the desired location on the teeth.

Referring now to FIG. 1, a system 10 is shown for generating an orthodontic template 12 for use in assisting a user to place appliances on teeth. The illustrated system 10 includes a computer 14 having a memory storing a virtual 3D model of the patient's dentition 16, including the upper and lower arches thereof. The virtual model of the dentition includes complete surface data for the lingual and labial surfaces of the teeth. The 3D model of the teeth is created using known scanning techniques, including in-vivo optical scanning or using radiographs such as MRI or CAT scans, scanning a model of the dentition, using laser scan of a plaster model, or using destructive scanning of a plaster model. The technique is not important.

The computer also executes an interactive CAD/CAM type treatment planning program that allows a user to place virtual brackets on virtual teeth. One suitable in-vivo scanner and treatment planning program is described in the published PCT application of OraMetrix, Inc., publication no. WO 01/80761. The entire content of that document, including the description and drawings of the scanner, the generation of virtual model of the dentition from scan data, the storage of brackets and placement of virtual brackets on teeth, and the treatment planning program, is expressly incorporated by reference herein. The computer 14 includes a video display 18 displaying the model of the teeth and brackets 20 placed thereon in an ideal tooth finish position. The computer 14 also includes user input devices comprising a keyboard 22 and mouse 24 that allow the user to use the program to change the position of the brackets and/or teeth during treatment planning.

The computer 14 is connected to a commercially available standard computer printer 26. The printer 26 is supplied with flexible material 25 in sheet form capable of forming the base material for the template 12. The flexible material 25 may comprise paper with an adhesive backing, translucent or clear plastic with or without an adhesive backing, or other materials. The material is capable of being printed with actual scale tooth outlines and marks indicating the location of the brackets on the teeth. In the example of FIG. 1, the material could be paper or plastic sheets with a pressure sensitive adhesive backing. Other techniques or equipment can be used to generate the templates.

Figure 8:
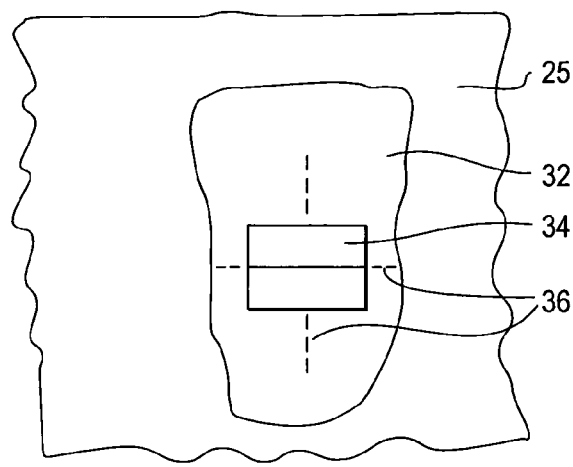
FIG. 8 is a plan view of a single tooth template similar to that shown in FIG. 2.

When the user has completed the interactive treatment planning and bracket placement on the computer, they would activate a suitable icon on the screen display 18 indicating "print bracket placement template." The computer then executes instructions to prepare a file containing the 2-dimensional actual scale representations of the outline of the teeth (arranged in a row so that the template 12 can be placed on the arch) and marks indicating the location and orientation of the brackets on each tooth surface. The process can be performed on a tooth-by-tooth basis for an entire arch. The template for an entire arch is shown in FIG. 1. The template 12 for a single tooth is shown in FIG. 8. The file is supplied to the printer 26 and the printer prints the template 12 as shown in FIG. 1.

Figure 2:
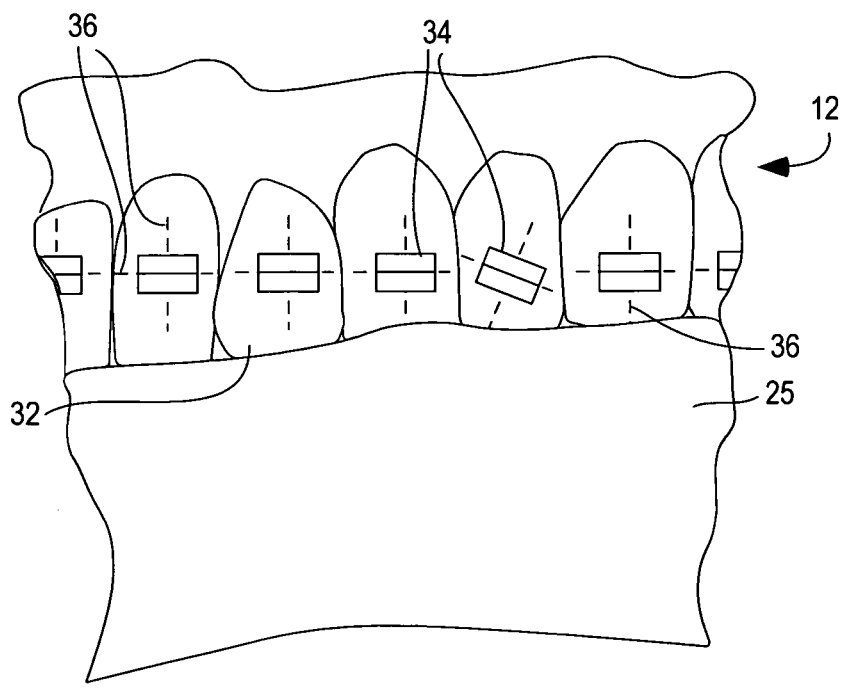
FIG. 2 is a more detailed view of a portion of the template for a set of teeth in the example of FIG. 1.
Figure 3:
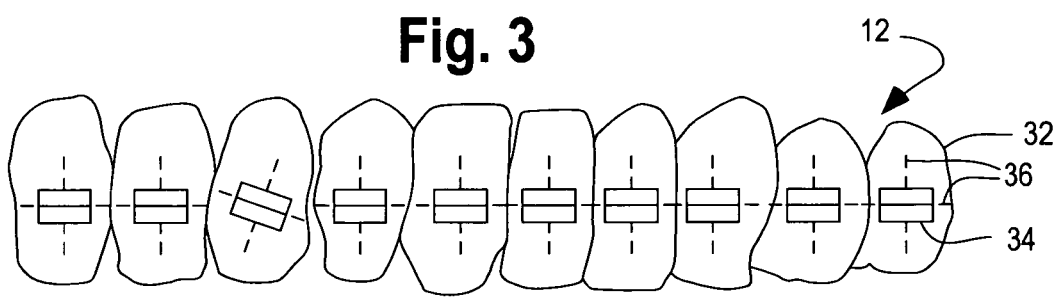
FIG. 3 is a view of the template of FIG. 1, after separation of the template from the rest of the sheet fed through the printer of FIG. 1. The template contains marks indicating the location of the brackets on the teeth in the ideal position.

FIG. 2 is a more detailed view of the template 12 of FIG. 1. The template 12 includes marks indicating the outline of the teeth 32, a mark 34 indicating the location of the bracket base, and bracket base angular orientation indicating marks 36 indicating the location and orientation of the bracket slot as an aid in positioning the bracket on the tooth correctly. The outline mark of the teeth 32 acts as a guide for installing the template 12 in a reference position such that the position of the bracket base mark 34 is in the proper position. The user then uses a suitable implement (e.g., scissors or knife) to cut out the template 12 from the sheet of material 25. The result is shown in FIG. 3. Alternatively, with a more advanced printing process, the template could be generated such that a perforation is provided at the location of the marks 32 indicating the outline of the teeth.

Figure 4:
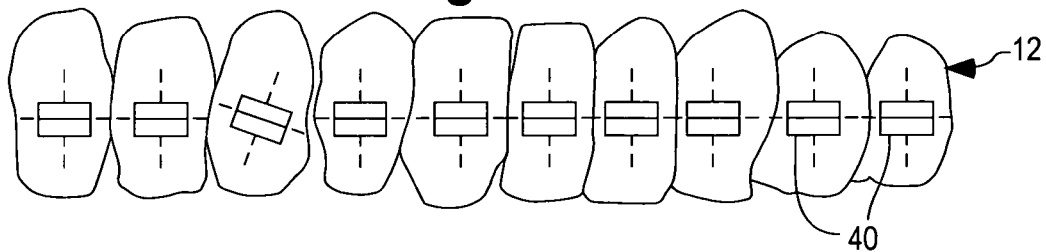
FIG. 4 is a view of the template of FIG. 3, after the user has punched out or otherwise removed the bracket base marks of FIG. 3.
Figure 5:
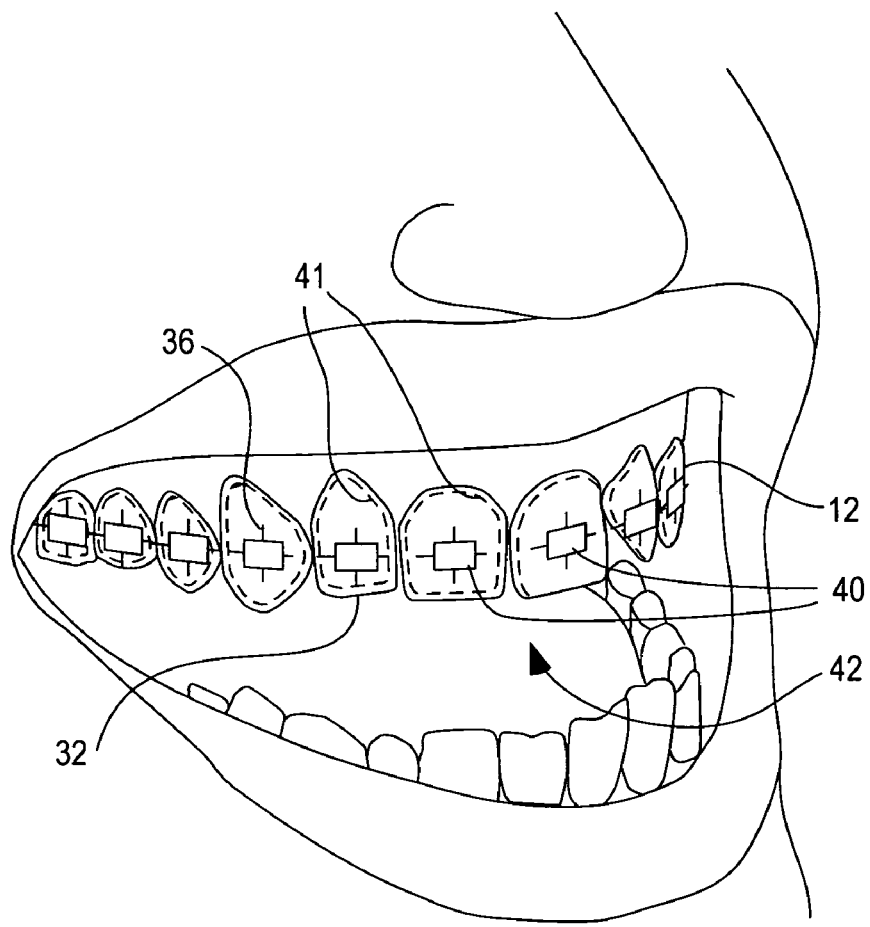
FIG. 5 is a illustration of the placement of the template of FIG. 4 onto the upper arch of a patient.

Either before or after separating the template 12 from the sheet of material, the user uses a punch or other implement (e.g., EXACTO™ knife) to remove the bracket base mark 34 so as to form a void in the template at the location of the bracket base. The result is shown in FIG. 4, with the voids indicated at 40. The user then applies the template 12 to the arch of the patient, for example the upper arch 42 as shown in FIG. 5. The template 12 has a tooth-facing surface that has an adhesive applied thereto so as to enable the template to be temporarily affixed to the surface of the teeth 41 as shown in FIG. 5. The positioning of the template to the tooth is somewhat critical in order to insure correct positioning of the void 40 relative to the tooth. The template needs to be adhered to the surface of the tooth or teeth 41 in a reference position such that the mark printed on the template, and eventually the void 40, accurately indicates the proper location for the bracket. The outline marks 32 indicating the outline of the teeth are one possible way of correctly positioning the template relative to the teeth. Other techniques could be developed by persons skilled in the art.

Figure 11:
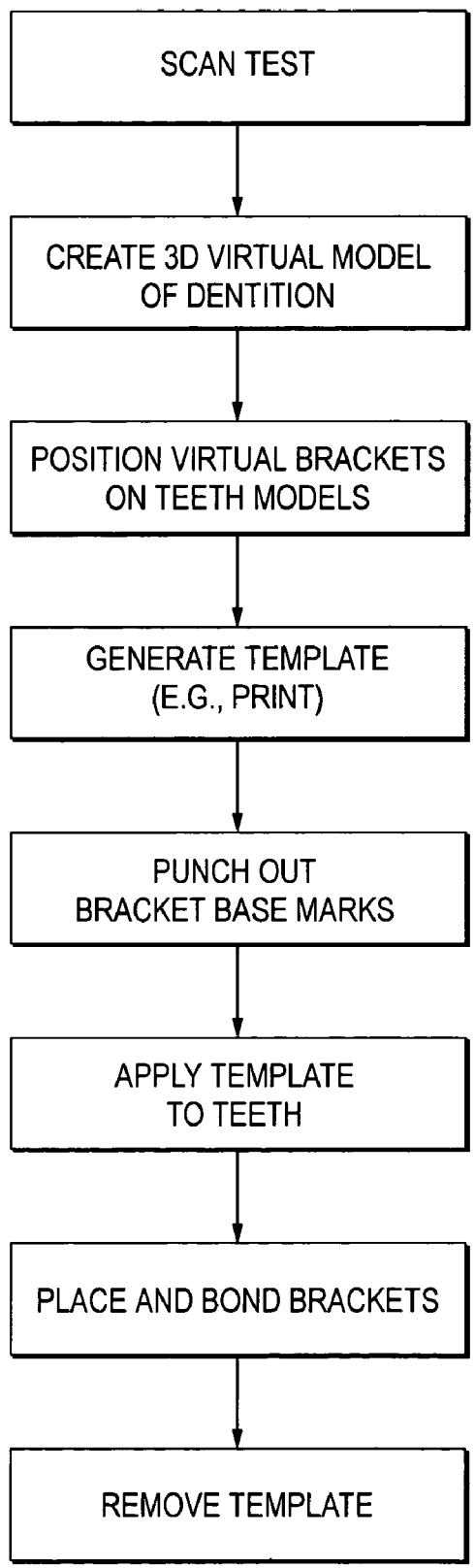
FIG. 11 is a flow chart showing the steps used to design, generate and use a template such as shown in FIGS. 2, 3 and 8; it will be appreciated that the steps shown in FIG. 11 will be slightly different when using other different types of templates, such as that shown in FIG. 6 or 9.

The orthodontist then bonds the brackets to the teeth using conventional direct bonding techniques at the location of the voids 40, using the guide marks 36 to insure the correct angular position of the slot. The orthodontic template 12 is then removed from the teeth 41, excess adhesive is removed and the patient is ready for fitting of the archwire. The above process is described in flow-chart form in FIG. 11.

An indirect approach is also possible. In this approach, the template is designed on a computer, and printed out as before. The template, with void for bonding the bracket and alignment marks as described above, is positioned on a plaster model of the tooth or teeth and the bracket is temporarily bonded to the plaster model. A jig for direct bonding the bracket to the patient's tooth is fabricated over the bracket+model according to techniques known in the art. The jig is then used to bond the bracket to the patient's tooth. This indirect approach may be preferred for situations where visual access of the template on the tooth in the patient's mouth is difficult, such as the molars. The positioning of the bracket on the plaster model using the template of course does not have this problem and the bracket can be precisely located using the template, and this precise location carried over to the patient's tooth using the bracket placement jig. Thus, in an alternative embodiment a method is provided for making a bracket placement jig for bonding a bracket to a tooth using a tooth template, comprising the steps of: a) generating a template for positioning a bracket on a tooth, the template comprising a flexible sheet of material and one or more marks indicating the position and orientation of a bracket base on the tooth in an ideal bracket placement position; b) forming a void in said template at the location of the bracket base; c) applying the template to the surface of a model of the tooth; d) placing a bracket on the tooth at the location of the void; e) temporarily bonding the bracket to the model; and f) fabricating a bracket placement jig for the bracket bonded to the model.

As noted above, in a preferred embodiment the flexible sheet 25 of material forming the template comprises a printed sheet of material, wherein one surface of the printed sheet of material (the tooth facing surface) comprises an adhesive material, either in an as-manufactured condition or an adhesive could be applied after the template is generated. In one possible embodiment, the flexible sheet of material is sized and shaped so as to fit over a single tooth of the patient. See, for example, the template shown in FIG. 8. Alternatively, the flexible sheet of material is sized and shaped so as to fit over a set of two or more teeth in an upper or lower arch of the patient, such as shown in FIG. 3 and described above, in which case the sheet of material comprises a plurality of marks, one set of mark 32 for each tooth to be fitted with an orthodontic bracket.

As noted above, in a preferred embodiment the orthodontic template is generated by a printer 26 coupled to a computer 14 containing a three-dimensional model of the teeth of the patient and the location of virtual brackets on the three-dimensional model. The computer converts the bracket location information in a format such that a two-dimensional printout of the tooth outline and the bracket base location and orientation enables the user to position the template on the tooth in a reference position and bond the bracket at the desired location.

In another possible embodiment, an orthodontic template for use in assisting a user in placing a bracket can be manufactured comprising a flexible sheet of material 25 sized and shaped so as to be placed onto at least one tooth of a set of teeth of a patient, with the sheet of material having a void 40 at the location and orientation of where a bracket is to be placed on the at least one tooth. The sheet can be initially printed with marks indicating the location of the bracket and the marks punched out or otherwise removed, or alternatively the sheet can be fabricated with voids already formed in the sheet. The voids 40 (FIG. 4) could be formed using any suitable mechanical, optical or electrical mechanism, such as with the use of mechanical punches, laser, etc. The sheet of material has a tooth-facing surface adapted to be adhered to a surface of the tooth in a reference position wherein the void accurately indicates the proper location for the bracket. The adhesive could be applied to the surface of the template before or after template is generated, or the adhesive could be applied to the tooth.

Figure 6:
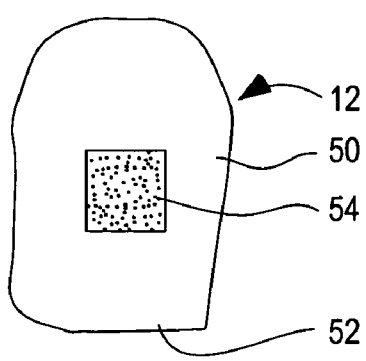
FIG. 6 is a plan view of an alternative type of template for a single tooth, in which the template includes a feature on one surface which is activated so as to leave a mark directly on the tooth surface.
Figure 7:
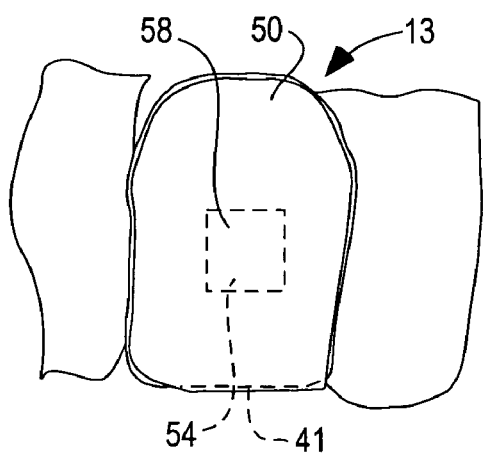
FIG. 7 is a plan view of the template of FIG. 6 applied in a reference position to a tooth prior to activation of the feature of FIG. 6.

Another embodiment is shown in FIG. 6. In this embodiment, the template 12 includes a flexible sheet of material 50 sized and shaped so as to be placed onto at least one tooth of a set of teeth of a patient. The sheet of material has a first, tooth-facing surface 52 and an opposite side. The tooth-facing surface 52 incorporates a mark indicating element 54 positioned at the location and orientation of where a bracket is to be placed on at least one tooth. The mark indicating element 54 is preferably made from a dyed material which, when activated by suitable mechanical or chemical means imparts a visually perceptible mark onto the tooth surface to indicate the proper location for the bracket. For example, the mark indicating element 54 may be a dye composition. When the template of FIG. 6 is applied to the tooth as shown in FIG. 7, the mark indicating element 54 is placed in direct contact with the tooth 41. The user rubs or scratches the opposite surface 58 of the template opposite the mark indicating element 54 so as to rub the dye onto the tooth surface. The template 12 is then removed, leaving the mark on the tooth 41. The user directly bonds the bracket to the tooth at the location of the mark.

Figure 12:
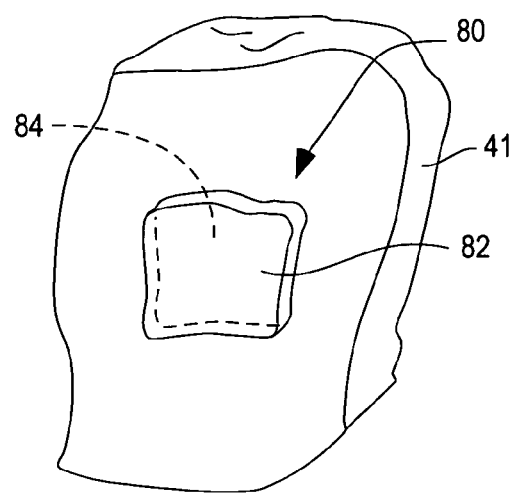
FIG. 12 is a perspective view of a shim used as an intermediary between a tooth and a bracket base to correctly position the bracket slot in three-dimensions; the process described in FIGS. 1-11 can be used to accurately locate bracket shims shown in FIG. 12.
Figure 12:
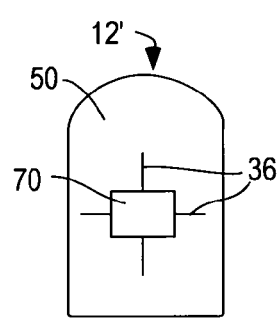
Figure 12:
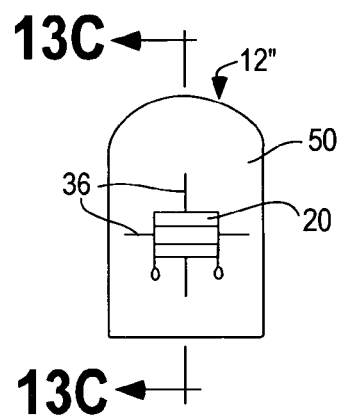
Figure 12:
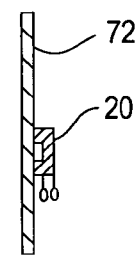
Figure 16A:
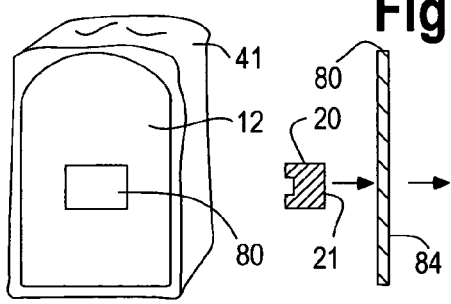
FIG. 16A is an illustration of a template positioned on a tooth with a shim shown in FIG. 12 bonded to the tooth in the location of a void formed in the template.
Figure 16B:
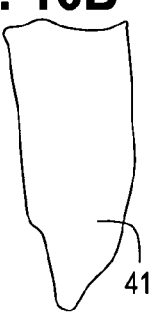
FIG. 16B is a side view showing the assembly of the shim of FIG. 12, a bracket and a tooth.

The templates of the present invention can be used to accurate place a three-dimensional shim to a bracket. Referring now to FIGS. 12, 16A and 16B, a shim 80 is provided which has a bracket base facing surface 82 and a tooth facing surface 84. The shim is made from any suitable rigid material, such as a ceramic material, metallic material, or cured adhesive material machined to the shape shown in FIG. 12. The three-dimensional surface configuration of the surfaces 82 and 84 is known with precision due to (1) the three-dimension surface shape of the associated tooth from the scanning of the dentition and (2) knowledge of the three-dimensional surface configuration of the bracket base 71 for which the shim 80 is to be used. This 3D surface configuration of the shim 80 is loaded into an appropriate milling machine or other apparatus and used to fabricate the shim 80 including surface 82 and 84. This surface configuration of the shim 80 allows the precise control of the positioning of the bracket 20 slot relative to the tooth 41, since there is no guess-work as to the positioning of the bracket relative to the tooth. With particular reference to FIG. 16B, the surface 71 of the bracket base fits or mates to the surface 82 of the shim, and the surface 84 fits precisely to the surface of the tooth 41 at the location where the shim 80 is bonded to the tooth 41.

The shim 80 is precisely bonded to the tooth 41 using the template 12 of this invention. Any of the previously described embodiments can be used to precisely position the shim on the tooth.

Figure 13D:
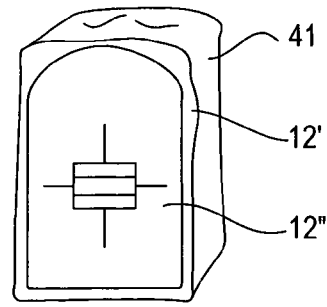

Still other embodiments are contemplated for bonding brackets or other orthodontic or dental appliances. In FIG. 13A, a template 12' consisting of a flexible sheet of material is provided with a void 70 and alignment marks 36. The template 12' is applied to the surface of the tooth. In FIG. 13B, a second template 12" is provided from a sheet 50 of transparent flexible material, having alignment marks 36 that correspond to (i.e., are in the same position as) the alignment marks of template 12' of FIG. 13A. The second template 12" has a tooth facing surface 72 shown in FIG. 13C to which is adhered a bracket at the proper location dictated by the alignment marks 36. In use, as shown in FIG. 13D, the first template 12' is applied to the tooth 41 in the predetermined position. Then, the second template 12" is applied over the first template 12' such that the bracket 20 is positioned in the void 70 of FIG. 13A. The bracket 20 is bonded to the tooth and then the templates 12', 12" are removed. Obviously, the procedure of FIGS. 13A-D can be used to position an optional shim as well.

Figure 14A:
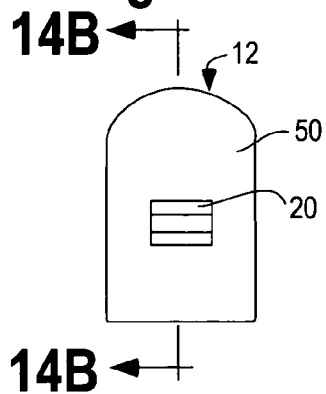
FIGS. 14A-B are several views of an alternative embodiment in which the bracket is carried in a void formed in a bracket carrier template.
Figure 14B:
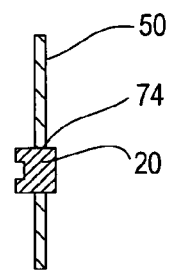
Figure 14C:
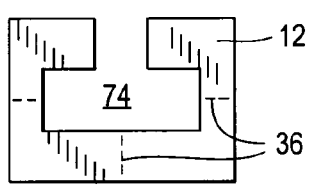
FIGS. 14C, 14D and 14E illustrate an alternative embodiment to that of FIGS. 14A-14B.
Figure 14D:
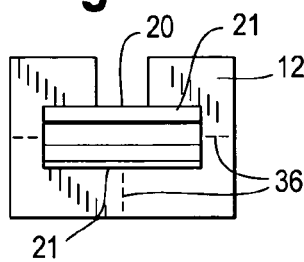
Figure 14E:
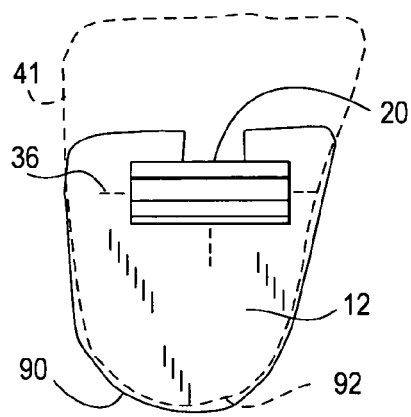

FIGS. 14A and 14B show an alternative embodiment in which the template 12 includes a flexible sheet 50 of transparent plastic material in which a bracket 20 is carried in a void formed or provided in the sheet 50, the void indicated at 74 in FIG. 14B. In FIGS. 14C, 14D and 14E, there is shown an alternative embodiment in which the template 12 is stamped out and made from a transparent plastic material and has a central void 74. The template 12 fits over the wings 21 of the bracket 12 and holds the bracket 20 in place. The template 12 and has alignment marks 36 for the bracket slot and marks 90 corresponding to anatomical features of the tooth 41, such as the outline of the tooth and/or outline of the incisal edge 92 of the tooth, that are superimposed on corresponding anatomical features on the tooth to insure correct template positioning. The bracket is then bonded in place as indicated in FIG. 14C. In this instance, the bracket template 12 does not have to be bonded to the tooth.

Figure 15:
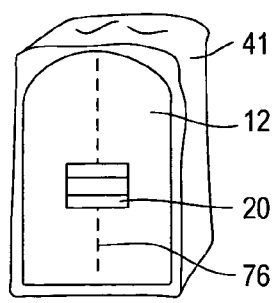
FIG. 15 is a view of a template having a perforation to assist in removing the template from the tooth after use.

FIG. 15 shows an embodiment in which a template 12 is positioned on a tooth 41 to correctly locate a bracket 20. The template 12 includes a perforation 76 designed to assist in the removal of the template 12 from the tooth after bonding the bracket 20.

Figure 17A:
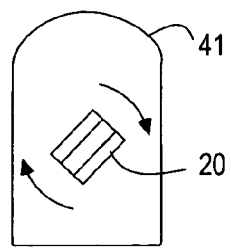
FIGS. 17A-C are an illustration of a tooth showing the various bracket positioning aspects provided by the templates of this invention.
Figure 17B:
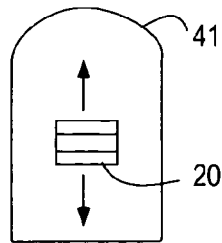
Figure 17C:
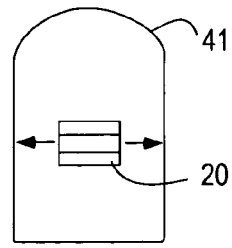

FIGS. 17A-17C show how the positioning of the bracket 20 on a tooth 41 can take into account angular positioning of the bracket (FIG. 17A), vertical positioning (FIG. 17B) and mesiodistal positioning (FIG. 17C). Any of these types of positioning strategies, or combinations thereof, are possible using the templates of this invention since they can be used to position a bracket virtually anywhere on a tooth and in any given position.

The templates can have additional landmarks or other guiding indicia, such as cross-hairs, marks indicating anatomical features, like the height of the gingival contour to help position the template. The template may have one sided or two sided pressure sensitive adhesive to temporarily affix the template to the tooth or a bracket, shim or other appliance to the template. The bracket templates can also be identified with tooth number and/or color coded as well for identification and ease of installation.

The bracket templates can be designed after bonding using traditional techniques. After the brackets have been bonded, an in-vivo scan of the patient is obtained and a virtual model of the dentition plus brackets stored in a computer. There is always a possibility of bracket loss and the templates of this invention can be designed and manufactured in case of loss; the brackets can be re-bonded in exactly the right position with the techniques of this invention.

The bracket templates can also be made clear in the area to be formed as a void, and opaque over the rest of the region covering the tooth. A laser can be used to etch the shape of the bracket on the tooth and this etching may serve two purposes, one for location of the bracket and second prepare the tooth surface for bonding. The clear area of the template can be burned by a laser to form the void, enabling bonding of the bracket to the tooth in the void region or to apply a treatment to a tooth (e.g., etching) in the void region. The opaque area serves to prevent spreading of the laser beam in the sheet of material forming the template.

Figure 9:
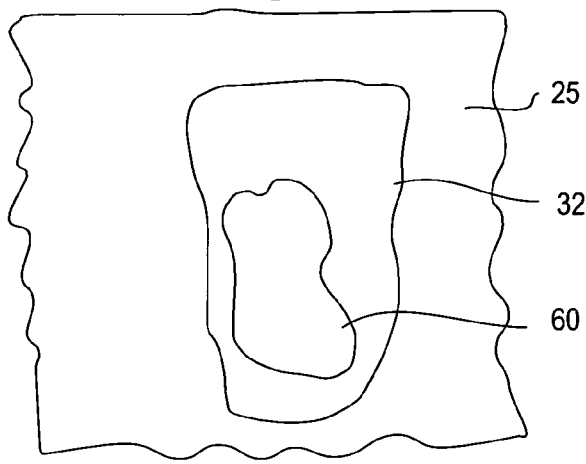
FIG. 9 is a plan view of a template that is used to precisely locate a given area for performing any of a variety of dental procedures on a tooth.
Figure 10:
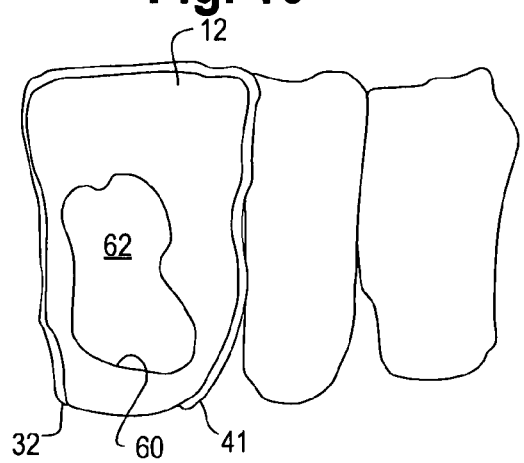
FIG. 10 is a plan view of the template of FIG. 9 applied to a tooth.

The templates have for other possible purposes besides bracket placement. The templates provide a masking feature whereby precise locations on a surface of a tooth can be identified for any relevant purpose in dentistry or orthodontics, such as identifying exact locations for etching using chemical means, varnishing, preparatory work for crowns or other dental prostheses (e.g., root canal, localization of the root chamber), and still others including localization of the treatment of cavities and locations for crowns and bridges. Basically, referring back to FIG. 1, the user creates 3-D models of the dentition using in-vivo scanning of the dentition, laser scanning of a plaster model of the teeth, or other technique. The model is stored in the computer. The user interface is provided with suitable tools to enable the user to mark or highlight specific areas on the tooth surface where some procedure (e.g., etching, varnishing, treatment of cavity) needs to be performed. Then, the user selects a "print template" icon and a file is created containing an actual scale representation of the tooth surface in two dimensions and the area selected by the user. This file is sent to the printer and a template such as shown in FIG. 9 is printed. The area 60 indicates the area on the tooth selected by the user for some procedure. The user cuts out the template along the edge of the tooth outline 32, cuts out with a suitable knife or other implement the area 60 to form a void in the area 60, and applies the template to the tooth 41, as shown in FIG. 10. As shown in FIG. 10, the tooth surface 62 is exposed for the procedure while the rest of the tooth is covered by the template 12. The tooth outline mark 32 enables the template 12 to be installed in a reference position such that the void 60 is in the proper location.

Figure 18:
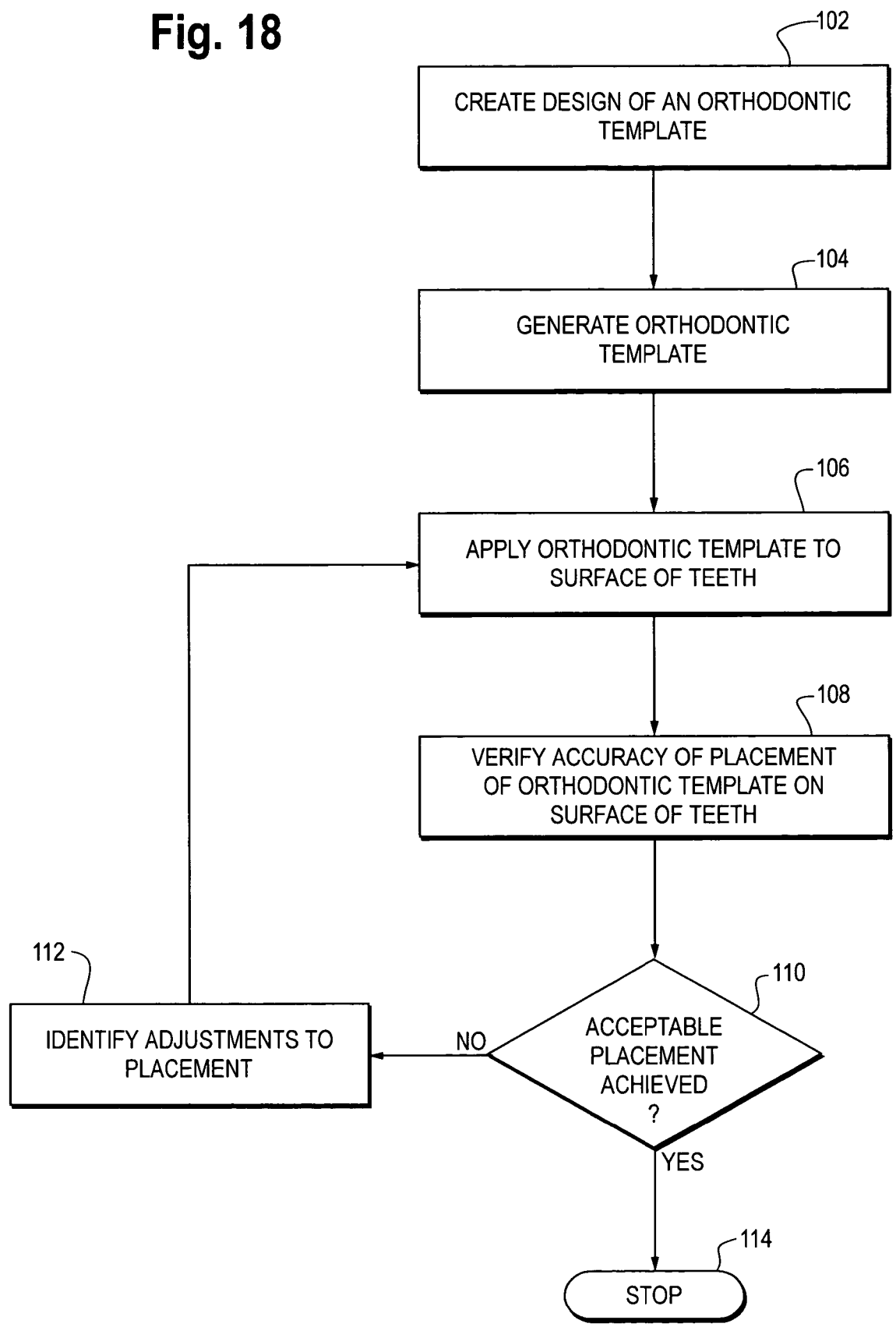
FIG. 18 is a flow chart showing the steps used in verifying the placement of an orthodontic template on the teeth of a patient according to a preferred embodiment of the invention.

FIG. 18 is a flow chart listing the steps of a method for verifying the accuracy of placement of an orthodontic template on the teeth of a patient according to a preferred embodiment of the invention. At step 102 a design of an orthodontic template is created through treatment planning using the computer 14 of FIG. 1 containing a three-dimensional virtual model of the teeth of a patient and the location of the virtual appliances on the three-dimensional virtual model. At step 104, the orthodontic template is generated using the design of the orthodontic template created at step 102. The template is made from a flexible sheet of material and indicates the outline of the teeth and marks for the position and orientation of the appliance on each tooth requiring an appliance. At step 106, the template is applied to the surface of the actual teeth of the patient. At step 108, the accuracy of the placement of the template on the actual teeth of the patient is verified using the computer 14. In order to verify the accuracy of the placement of the template on the actual teeth of the patient, an image of the dentition of the patient with the template attached to the actual teeth is taken and stored in the computer 14. The image of the dentition of the patient with the template attached to the actual teeth is then transformed into a virtual, digital model and digitally compared with the template design placed on the virtual three-dimensional model of the teeth of the patient using the computer 14. The image of the dentition of the patient with the template applied to the actual teeth of the patient is obtained by in-vivo scanning or digital photographs or other similar means. Then at step 110 a determination is made as to weather or not the placement is acceptable. If the comparison reveals any unacceptable discrepancy between the placement of the template on the actual teeth and the desired placement of the template, then at step 112 the required adjustments to the placement of the template are identified in the computer 14 and the process returns to step 106. On the other hand, if at step 110 the placement of the template on the actual teeth of the patient is determined to be acceptable, then the process stops at step 114.

Figure 19A:
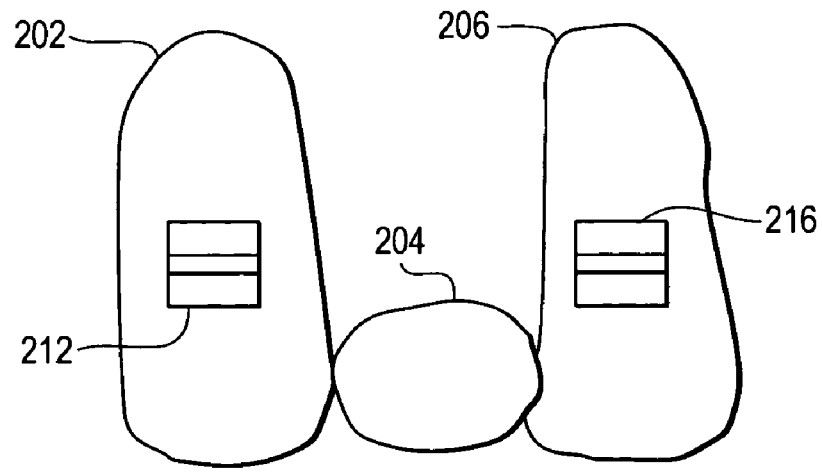
FIG. 19A illustrates a partially erupted tooth unable to receive a bracket where as FIG. 19B illustrates the same tooth in a fully erupted state capable of receiving a bracket.
Figure 19B:
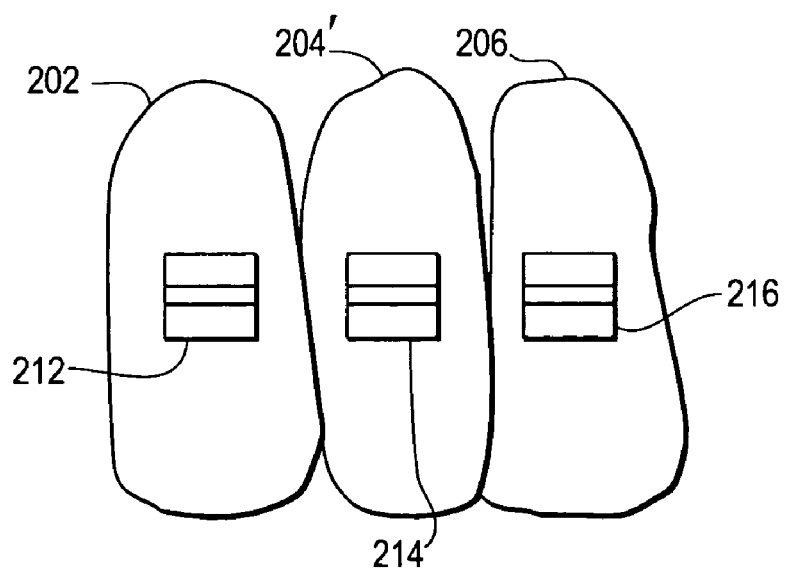

In another preferred embodiment of the invention, a method of making an orthodontic template for a patient for use in assisting a user in placing an appliance on a designated tooth which was previously partially erupted and unable to receive an appliance is provided. The underlying scenario is illustrated as an example by FIGS. 19A and 19B. FIG. 19A shows tooth 202 and tooth 206 which are fully erupted and able to receive brackets 212 and 216. However, tooth 204 is only partially erupted and there is not sufficient room to place a bracket on this tooth. Some time later on, tooth 204 either fully erupts or erupts to a level having sufficient surface to receive a bracket. This situation is illustrated by FIG. 19B. Here it is possible to place a bracket 214 on tooth 204'. Tooth 204' illustrates a fully erupted state of tooth 204 in FIG. 19A. In FIGS. 19A and 19B, the bracket is used simply as an example; however, the discussion equally applies to any other orthodontic appliance. Using the disclosure of this invention it is possible to devise a template for placing an appliance on the previously partially erupted tooth that has now sufficiently matured. The template design method takes into account the existing appliances on other teeth. The method comprises the steps of: (a) obtaining a three-dimensional virtual model of a patient comprising a designated tooth void of an appliance and the remaining teeth wherein each of a plurality of the remaining teeth has an appliance attached thereto; (b) storing the three-dimensional virtual model in a computer, the computer having instructions foe treatment planning and a library of virtual appliances; (c) positioning a virtual appliance on the designated tooth through treatment planning using the three-dimensional virtual model, wherein the virtual appliance is selected from the library of virtual appliances; (d) creating a design of an orthodontic template using the positioning of the virtual appliance on the designated tooth using the computer; (e) generating said orthodontic template from a flexible sheet of material using the design of the orthodontic template; the template indicating the outline of the designated tooth; and (f) sizing and shaping the flexible sheet of material so as to be able to be placed onto the designated tooth of the patient, the sheet of material having one or more marks indicating the location and orientation of where the appliance is to be placed on the designated tooth; the sheet of material having a tooth-facing surface adapted for positioning on the surface of said designated tooth in a reference position wherein the one or more marks accurately indicate the proper location for said appliance. As noted earlier, the method is particularly useful where the designated tooth was previously only partially erupted and therefore unable to receive an appliance. The virtual three-dimensional model is created using images obtained through in-vivo scanning the patient. The images include the patient's teeth as well as existing appliances on the remaining teeth.

Modifications to the illustrated embodiments are within the scope of the invention. The scope is to be determined by reference to the appended claims, interpreted in light of the foregoing specification.

I claim:

1. A method for verifying the accuracy of the placement of an orthodontic template on the teeth of a patient, comprising the steps of:
 a) creating a design of an orthodontic template through treatment planning using a computer containing a three-dimensional virtual model of the teeth of a patient and the location of virtual appliances on said three-dimensional virtual model;
 b) generating said orthodontic template using said design of the orthodontic template; said template comprising a flexible sheet of material and said template indicating the outline of the teeth and marks indicating the position and orientation of the appliance on each tooth;
 c) applying said template to the surface of the actual teeth of said patient;
 d) verifying the accuracy of the placement of said template on the actual teeth of said patient using said computer; and
 e) adjusting the placement of said template on the actual teeth of said patient until an acceptable placement of the template is achieved.

2. The method of claim 1, wherein the step d) of verifying the accuracy of the placement of said template on the actual teeth of said patient comprises taking an image of the dentition of the patient with the template placed upon the actual teeth; storing said image in said computer; and digitally comparing said image with said template design placed on said virtual three-dimensional model of the teeth of said patient.

3. The method of claim 2; wherein said image of the dentition of said patient with said template placed upon the actual teeth is taken using in-vivo scanning.

4. The method of claim 2; wherein said image of the dentition of said patient with said template placed upon the actual teeth is taken with digital photographs.

5. The method of claim 1, wherein said flexible sheet of material having said mark comprises a printed sheet of material, wherein one surface of said printed sheet of material comprises an adhesive material.

6. The method of claim 1, wherein said flexible sheet of material is sized and shaped so as to fit over a single tooth of said patient.

7. The method of claim 1, wherein said flexible sheet of material is sized and shaped so as to fit over a set of two or more teeth in an upper or lower arch of said patient, and wherein said sheet of material comprises a plurality of marks, one mark for each tooth in said set of two or more teeth to be fitted with an appliance.

8. The method of claim 1, wherein said appliance comprises a bracket and said mark comprises a first portion comprising a bracket base location indicating mark and a second portion comprising a bracket base angular orientation indicating mark.

9. The method of claim 1, wherein said appliance is selected from the group of appliances comprising bracket shims and orthodontic brackets, and wherein said orthodontic template is generated by a printer coupled to said computer containing said three-dimensional virtual model of the teeth of said patient and the location of virtual brackets on said three-dimensional model.

10. A method of making an orthodontic template for a patient for use in assisting a user in placing an appliance on a designated tooth void of an appliance whereas each of a plurality of the remaining teeth has an appliance attached thereto, comprising the steps of:
 obtaining a three-dimensional virtual model of a patient comprising a designated tooth void of an appliance and the remaining teeth wherein each of a plurality of the remaining teeth has an appliance attached thereto;
 storing said three-dimensional virtual model in a computer, said computer having instructions foe treatment planning and a library of virtual appliances;

positioning a virtual appliance on said designated tooth through treatment planning using said three-dimensional virtual model, wherein said virtual appliance is selected from said library of virtual appliances;

creating a design of an orthodontic template using said positioning of said virtual appliance on said designated tooth using said computer;

generating said orthodontic template from a flexible sheet of material using said design of said orthodontic template; said template indicating the outline of said designated tooth; and sizing and shaping said flexible sheet of material so as to be able to be placed onto said designated tooth of said patient, said sheet of material having one or more marks indicating the location and orientation of where said appliance is to be placed on said designated tooth;

said sheet of material having a tooth-facing surface adapted for positioning on the surface of said designated tooth in a reference position wherein said one or more marks accurately indicate the proper location for said appliance.

11. The method of claim 10, wherein said designated tooth was previously only partially erupted and therefore unable to receive an appliance.

12. The method of claim 10, wherein said virtual three-dimensional model is created using images obtained through in-vivo scanning said patient.

13. The method of claim 10, wherein said flexible sheet of material having said mark comprises a printed sheet of material, wherein one surface of said printed sheet of material comprises an adhesive material.

14. The method of claim 10, wherein said flexible sheet of material is sized and shaped so as to fit over said designated tooth of said patient.

15. The method of claim 10, wherein said appliance comprises a bracket and said mark comprises a first portion comprising a bracket base location indicating mark and a second portion comprising a bracket base angular orientation indicating mark.

16. The method of claim 10, wherein said appliance is selected from the group of appliances comprising bracket shims and orthodontic brackets, and wherein said orthodontic template is generated by a printer coupled to said computer containing said three-dimensional virtual model of said patient and the location of virtual bracket on said three-dimensional model.

* * * * *